(12) United States Patent
Houben et al.

(10) Patent No.: US 8,620,424 B2
(45) Date of Patent: Dec. 31, 2013

(54) METHOD AND APPARATUS FOR PROVIDING EXTRA SYSTOLIC STIMULATION

(75) Inventors: Richard P. M. Houben, Lanaken (BE);
Berthold Stegemann, Aachan (DE);
Richard Cornelussen, Maastricht (NL)

(73) Assignee: Medtronic, Inc., Minneapolis, MN (US)

( * ) Notice: Subject to any disclaimer, the term of this patent is extended or adjusted under 35 U.S.C. 154(b) by 1257 days.

(21) Appl. No.: 11/742,011

(22) Filed: Apr. 30, 2007

(65) Prior Publication Data
US 2008/0269815 A1 Oct. 30, 2008

(51) Int. Cl.
*A61N 1/362* (2006.01)

(52) U.S. Cl.
USPC ..................................... 607/9; 607/7; 607/8

(58) Field of Classification Search
USPC ....................................................... 607/7–9
See application file for complete search history.

(56) References Cited

U.S. PATENT DOCUMENTS

| | | | |
|---|---|---|---|
| 3,857,399 A | 12/1974 | Zacouto | |
| 3,939,844 A | 2/1976 | Pequignot | |
| 4,944,298 A | 7/1990 | Sholder | |
| 5,213,098 A * | 5/1993 | Bennett et al. | 607/18 |
| 5,411,531 A | 5/1995 | Hill et al. | |
| 5,800,464 A | 9/1998 | Kieval | |
| 6,738,667 B2 | 5/2004 | Deno et al. | |
| 7,024,243 B1 | 4/2006 | Bornzin et al. | |
| 7,096,064 B2 | 8/2006 | Deno et al. | |
| 7,130,684 B2 | 10/2006 | Mulligan et al. | |
| 7,289,850 B2 | 10/2007 | Burnes et al. | |
| 2004/0049235 A1 * | 3/2004 | Deno et al. | 607/9 |
| 2004/0158292 A1 | 8/2004 | Sheldon et al. | |
| 2004/0220640 A1 | 11/2004 | Burnes et al. | |
| 2005/0075674 A1 | 4/2005 | Zillmer et al. | |
| 2005/0075676 A1 | 4/2005 | Deno et al. | |
| 2005/0075677 A1 | 4/2005 | Gannion et al. | |
| 2007/0073352 A1 * | 3/2007 | Euler et al. | 607/23 |
| 2008/0077187 A1 | 3/2008 | Levin et al. | |
| 2010/0094370 A1 | 4/2010 | Levin et al. | |
| 2010/0198293 A1 | 8/2010 | Kaiser et al. | |
| 2010/0298901 A1 | 11/2010 | Sommer et al. | |

FOREIGN PATENT DOCUMENTS

| | | |
|---|---|---|
| WO | 9725098 | 7/1997 |
| WO | 0158518 C1 | 8/2001 |
| WO | 02053026 A2 | 7/2002 |

OTHER PUBLICATIONS

International Preliminary Report on Patentability from international application No. PCT/US2011/033981, dated May 10, 2013, 9 pp.
International Search Report and Written Opinion of international application No. PCT/US2011/033981, dated Aug. 2, 2011, 12 pp.

* cited by examiner

*Primary Examiner* — Rex R Holmes
(74) *Attorney, Agent, or Firm* — Reed A. Duthler; Stephen W. Bauer (57) ABSTRACT

An implantable medical device and associated method control the delivery of extra systolic stimulation by determining a coupling interval, setting an extra systolic interval in response to the coupling interval; and delivering a supraventricular stimulation pulse upon expiration of the extra systolic interval. The supraventricular stimulation pulse evokes a depolarization that is conducted to the ventricles occurring at a ventricular coupling interval relative to a ventricular event.

5 Claims, 7 Drawing Sheets

METHOD AND APPARATUS FOR PROVIDING EXTRA SYSTOLIC STIMULATION

TECHNICAL FIELD

The invention relates generally to implantable medical devices and, in particular, to a device and associated method for delivering extra systolic stimulation therapy.

BACKGROUND

Post-extra systolic potentiation (PESP) is a property of cardiac myocytes that results in enhanced mechanical function of the heart on the beats following an extra systolic stimulus delivered early after either an intrinsic or pacing-induced systole. The magnitude of the enhanced mechanical function is strongly dependent on the timing of the extra systole relative to the preceding intrinsic or paced systole. When correctly timed, an extra systolic stimulation pulse causes an electrical depolarization of the heart but the attendant mechanical contraction is absent or substantially weakened. The contractility of the subsequent cardiac cycles, referred to as the post-extra systolic beats, is increased as described in detail in commonly assigned U.S. Pat. No. 5,213,098 issued to Bennett et al., incorporated herein by reference in its entirety.

Generally, PESP therapy has been proposed in two forms, "paired pacing" and "coupled pacing". In paired pacing, the primary systole is a paced event followed by a paced extra systole delivered in the same chamber as the paced event, at a selected extra systolic interval (ESI) following the primary pacing pulse. In coupled pacing, the primary systole is an intrinsic depolarization followed by an extra systolic pacing pulse delivered in the same chamber as the sensed intrinsic depolarization at a selected ESI following the primary depolarization.

As noted, the degree of mechanical augmentation on post-extra systolic beats depends strongly on the timing of the extra systole following a first depolarization. If the ESI is too long, the PESP effects are not achieved because a normal mechanical contraction takes place in response to the extra systolic stimulus. As the ESI is shortened, a maximal effect is reached when the ESI is slightly longer than the physiological refractory period. An electrical depolarization occurs without a mechanical contraction or with a substantially weakened contraction. When the ESI becomes too short, the stimulus falls within the absolute refractory period and no depolarization occurs. As such, methods for controlling the ESI and for delivering pacing pulses in a manner that achieves an optimal PESP effect are needed.

DETAILED DESCRIPTION

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

The present invention relates to providing an implantable system for delivering an extra systolic stimulation (ESS) therapy. In one embodiment, electrical stimulation pulses are delivered to achieve post extra systolic potentiation (PESP) by controlling the time of extra systolic depolarizations relative to primary systolic depolarizations. In particular, embodiments of the invention include methods for controlling the delivery of supraventricular extra systolic stimulation pulses for causing an intrinsically conducted depolarization to occur in the ventricles at a desired coupling interval relative to a ventricular event. The conducted depolarization resulting from the supraventricular pulse may precede an intrinsic depolarization originating in the atrium and conducted to the ventricles such that the conducted supraventricular evoked response becomes the primary systole and the intrinsic depolarization originating in the atria and conducted to the ventricles becomes the extra systole. Alternatively, the supraventricular stimulation pulse is delivered to evoke a response that is conducted to the ventricles as an extra systole following a primary systole, intrinsic or evoked.

As used herein, "supraventricular" refers to any location in the atria or anywhere along the myocardial conduction system above and including the bundle of His. In past practice, methods for delivering extra systolic stimulation therapy in the ventricles involved delivering a ventricular stimulation pulse to the ventricles for evoking the extra systole. By providing a supraventricular stimulation pulse and allowing the resulting evoked depolarization to be conducted to the ventricles via the normal, intrinsic conduction system, a more optimal post-extra systolic potentiation response may be achieved. An intrinsically conducted extra systole is expected to provide a more coordinated depolarization of the ventricular myocardium as compared to apical paced extra systoles. The more coordinated or natural depolarization of the ventricles on the extra systole may enhance the overall PESP effects. As such, a system and associated methods will be described herein for providing intrinsically conducted extra systoles involving the delivery of a supraventricular stimulation pulse.

Figure 1:
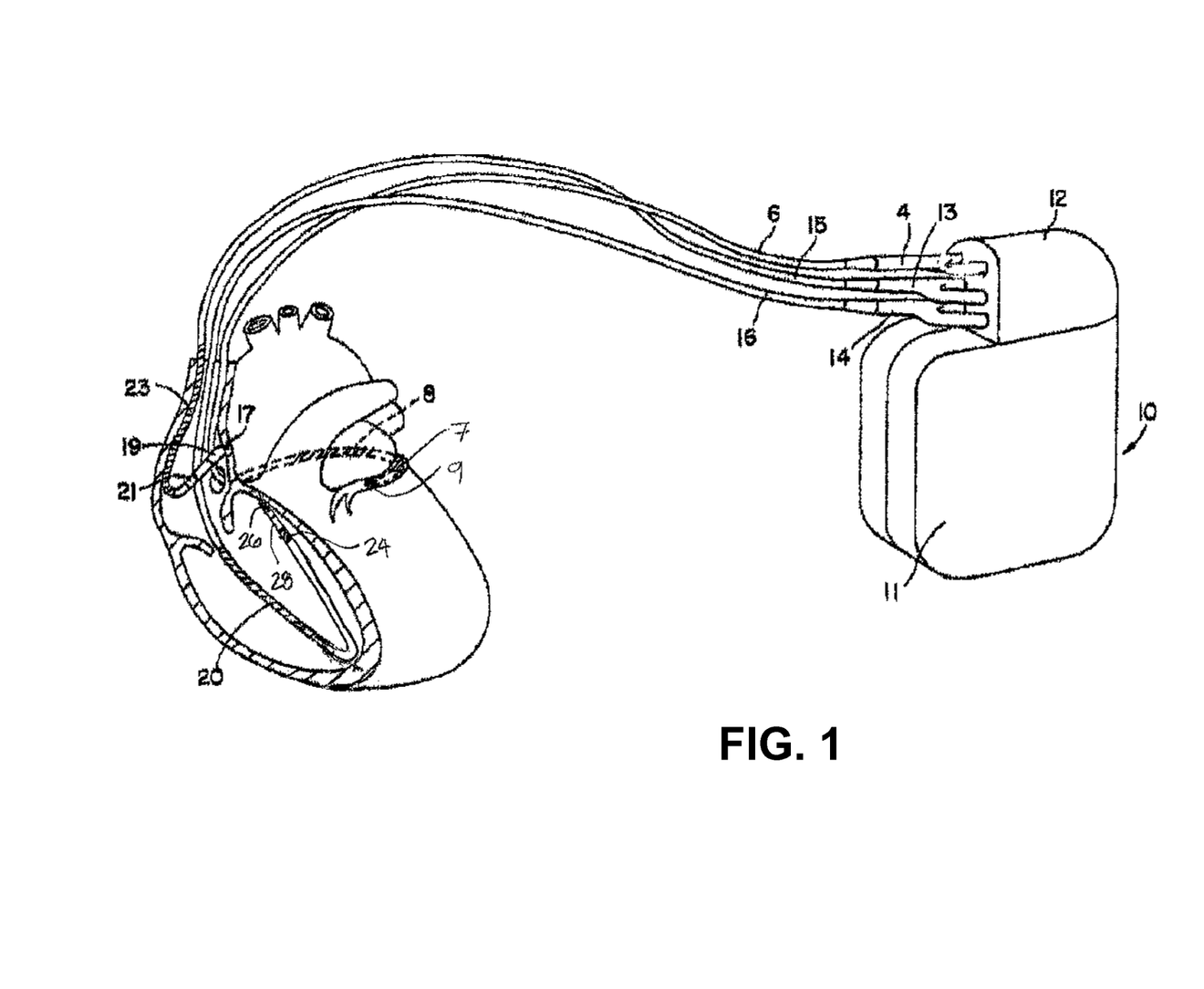
FIG. 1 is a schematic diagram of an implantable medical device (IMD) coupled to a patient's heart.

FIG. 1 is a schematic diagram of an implantable medical device (IMD) coupled to a patient's heart by way of three cardiac leads 6, 15, and 16. IMD 10 is capable of receiving and processing cardiac electrical signals and delivering electrical stimulation pulses for ESS and may additionally be capable of delivering other cardiac pacing, cardioversion and defibrillation therapies. IMD 10 includes a connector block 12 for receiving the proximal end of a right ventricular lead 16, a right atrial lead 15 and a coronary sinus lead 6, used for positioning electrodes for sensing and stimulating in three or four heart chambers.

In FIG. 1, the right ventricular lead 16 is positioned such that its distal end is in the right ventricle for sensing right ventricular cardiac signals and delivering electrical stimulation pulses in the right ventricle. Right ventricular lead 16 is provided with a ring electrode 24, a tip electrode 26 optionally mounted retractably within an electrode head 28, and a coil electrode 20, each of which are connected to an insulated conductor within the body of lead 16. In one embodiment, right ventricular lead 16 is adapted for deployment in the right ventricle such that tip electrode 26 is positioned relative to the bundle of His for delivering supraventricular extra systolic stimulation pulses to the His bundle. Right ventricular lead 16 may include other electrodes for pacing and sensing within the right ventricle. The proximal end of the insulated conductors are coupled to corresponding connectors carried by connector 14 at the proximal end of lead 16 for electrical connection to IMD 10.

The right atrial lead 15 is positioned such that its distal end is in the vicinity of the right atrium and the superior vena cava. Lead 15 is equipped with a ring electrode 21, a tip electrode 17, optionally mounted retractably within electrode head 19, and a coil electrode 23 for providing sensing and electrical stimulation therapies in the right atrium. In one embodiment, supraventricular pulses during an ESS therapy are delivered in the right atrium using atrial lead 15. The ring electrode 21, the tip electrode 17 and the coil electrode 23 are each connected to an insulated conductor with the body of the right atrial lead 15. Each insulated conductor is coupled at its proximal end to a connector carried by bifurcated connector 13.

The coronary sinus lead 6 is advanced within the vasculature of the left side of the heart via the coronary sinus and great cardiac vein. The coronary sinus lead 6 is shown in the embodiment of FIG. 1 as having a defibrillation coil electrode 8 that may be used in combination with either the coil electrode 20 or the coil electrode 23 for delivering electrical shocks for cardioversion and defibrillation therapies. Coronary sinus lead 6 is also equipped with a distal tip electrode 9 and ring electrode 7 for sensing functions and delivering stimulation pulses in the left ventricle of the heart. The coil electrode 8, tip electrode 9 and ring electrode 7 are each coupled to insulated conductors within the body of lead 6, which provides connection to the proximal bifurcated connector 4. In alternative embodiments, lead 6 may additionally include ring electrodes positioned for left atrial sensing and stimulation functions. Such left atrial electrodes may be used for delivering supraventricular pulses during an ESS therapy.

The electrodes 17 and 21, 24 and 26, and 7 and 9 may be used in sensing and stimulation as bipolar pairs, commonly referred to as a "tip-to-ring" configuration, or individually in a unipolar configuration with the device housing 11 serving as the indifferent electrode, commonly referred to as the "can" or "case" electrode. IMD 10 is capable of delivering high-voltage cardioversion and defibrillation therapies. As such, device housing 11 may also serve as a subcutaneous defibrillation electrode in combination with one or more of the defibrillation coil electrodes 8, 20 or 23 for defibrillation of the atria or ventricles.

It is recognized that alternate lead systems may be substituted for the three lead system illustrated in FIG. 1. For example, lead systems including one or more unipolar, bipolar and/or mulitpolar leads may be configured for sensing cardiac electrical signals and delivering electrical stimulation pulses to the heart. It is contemplated that subcutaneous ECG electrodes could be included in the implantable system, mounted on subcutaneous leads extending from IMD 10 and/or incorporated on the housing 11.

Figure 2:
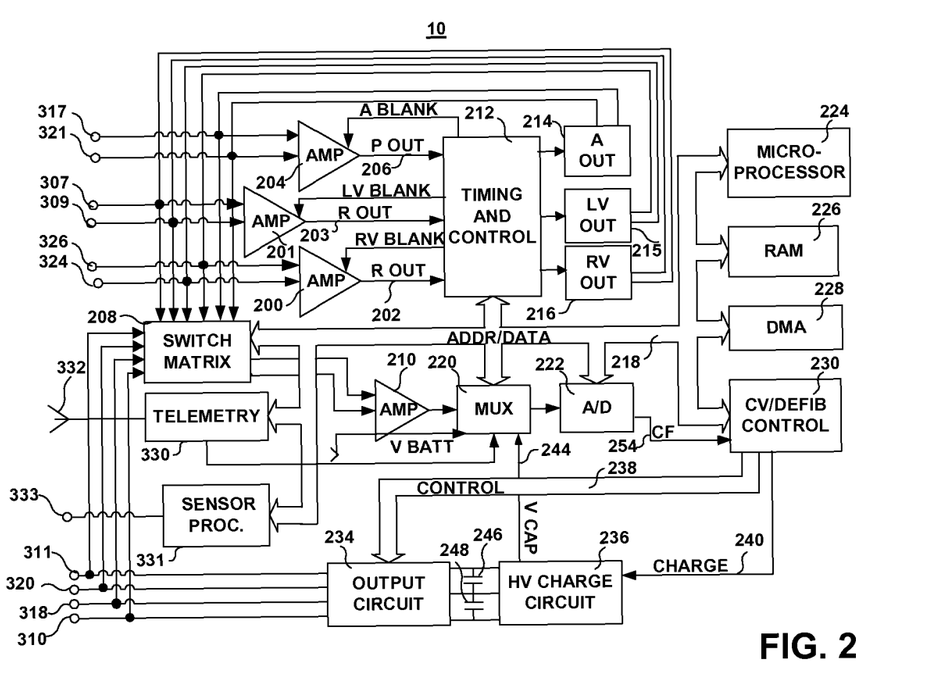
FIG. 2 is a functional block diagram of an IMD.

FIG. 2 is a functional block diagram of an IMD. The embodiment shown in FIG. 2 is a microprocessor-controlled device, but other control circuitry may be used such as dedicated digital or analog circuitry. With regard to the electrode system illustrated in FIG. 1, IMD 10 is provided with a number of connection terminals for achieving electrical connection to the leads 6, 15, and 16 and their respective electrodes. The connection terminal 311 provides electrical connection to the housing 11 for use as the indifferent electrode during unipolar stimulation or sensing. The connection terminals 320, 310, and 318 provide electrical connection to coil electrodes 20, 8 and 23 respectively. Each of these connection terminals 311, 320, 310, and 318 are coupled to the high voltage output circuit 234 to facilitate the delivery of high energy shocking pulses to the heart using one or more of the coil electrodes 8, 20, and 23 and optionally the housing 11. Connection terminals 311, 320, 310 and 318 are further connected to switch matrix 208 such that the housing 11 and respective coil electrodes 20, 8, and 23 may be selected in desired configurations for various sensing and stimulation functions of IMD 10.

The connection terminals 317 and 321 provide electrical connection to the tip electrode 17 and the ring electrode 21 positioned in the right atrium. The connection terminals 317 and 321 are further coupled to an atrial sense amplifier 204 for sensing atrial signals such as P-waves. The connection terminals 326 and 324 provide electrical connection to the tip electrode 26 and the ring electrode 24 positioned in the right ventricle. The connection terminals 307 and 309 provide electrical connection to tip electrode 9 and ring electrode 7 positioned in the coronary sinus. The connection terminals 326 and 324 are further coupled to a right ventricular (RV) sense amplifier 200, and connection terminals 307 and 309 are further coupled to a left ventricular (LV) sense amplifier 201 for sensing right and left ventricular signals, respectively.

The atrial sense amplifier 204 and the RV and LV sense amplifiers 200 and 201 may correspond to automatic gain controlled amplifiers with adjustable sensing thresholds. Generally, whenever a signal received by atrial sense amplifier 204 exceeds an atrial sensing threshold, a signal is generated on output signal line 206. P-waves are typically sensed based on a P-wave sensing threshold for use in detecting an atrial rate. Whenever a signal received by RV sense amplifier 200 or LV sense amplifier 201 that exceeds an RV or LV sensing threshold, respectively, a signal is generated on the corresponding output signal line 202 or 203. R-waves are typically sensed based on an R-wave sensing threshold for use in detecting a ventricular rate.

Switch matrix 208 is used to select which of the available electrodes are coupled to a wide band amplifier 210 for use in digital signal analysis. Selection of the electrodes is controlled by the microprocessor 224 via data/address bus 218. The selected electrode configuration may be varied as desired for the various sensing, pacing, cardioversion, defibrillation and ESS functions of the IMD 10. Signals from the electrodes selected for coupling to bandpass amplifier 210 are provided to multiplexer 220, and thereafter converted to multi-bit digital signals by A/D converter 222, for storage in random access memory 226 under control of direct memory access circuit 228. Microprocessor 224 may employ digital signal analysis techniques to characterize the digitized signals stored in random access memory 226 to recognize and classify the patient's heart rhythm.

The telemetry circuit 330 receives downlink telemetry from and sends uplink telemetry to an external programmer via an antenna 332. Data to be uplinked to the programmer and control signals for the telemetry circuit are provided by microprocessor 224 via address/data bus 218. Received telemetry is provided to microprocessor 224 via multiplexer 220.

The remainder of the circuitry illustrated in FIG. 2 is generally dedicated to providing ESS, cardiac pacing, cardioversion and defibrillation therapies. The timing and control circuitry 212 includes programmable digital counters which control the basic time intervals associated with ESS, various single, dual or multi-chamber pacing modes, or anti-tachycardia pacing therapies delivered in the atria or ventricles. Timing and control circuitry 212 also determines the amplitude of the cardiac stimulation pulses under the control of microprocessor 224.

During pacing, escape interval counters within timing and control circuitry 212 are reset upon sensing of RV R-waves, LV R-waves or atrial P-waves as indicated by signals on lines 202, 203 and 206, respectively. In accordance with the selected mode of pacing, pacing pulses are generated by atrial output circuit 214, right ventricular output circuit 216, and left ventricular output circuit 215. The escape interval counters are reset upon generation of pacing pulses, and thereby control the basic timing of cardiac pacing functions, which may include bradycardia pacing, cardiac resynchronization therapy, and anti-tachycardia pacing.

The durations of the escape intervals are determined by microprocessor 224 via data/address bus 218. The value of the count present in the escape interval counters when reset by sensed R-waves or P-waves can be used to measure R-R intervals and P-P intervals for detecting the occurrence of a variety of arrhythmias.

Timing and control 212 further controls the delivery of supraventricular stimulation pulses delivered according to an extra systolic interval (ESI) relative to sensed or paced supraventricular events, e.g. a sensed P-wave or an atrial pacing pulse. The supraventricular pulse may be delivered to any supraventricular location, in an atrial heart chamber or to the His Bundle. The desired ESI or other timing intervals derived therefrom are used in controlling the delivery of supraventricular stimulation pulses by IMD 10 and are automatically adjusted by IMD 10 to evoke an intrinsically-conducted ventricular extra systole as will be described in greater detail below. The output circuits 214, 215 and 216 are coupled to the desired stimulation electrodes for delivering cardiac pacing therapies and ESS via switch matrix 208.

The microprocessor 224 includes associated ROM in which stored programs controlling the operation of the microprocessor 224 reside. A portion of the memory 226 may be configured as a number of recirculating buffers capable of holding a series of measured R-R or P-P intervals for analysis by the microprocessor 224 for predicting or diagnosing an arrhythmia.

In response to the detection of tachycardia, anti-tachycardia pacing therapy can be delivered by loading a regimen from microcontroller 224 into the timing and control circuitry 212 according to the type of tachycardia detected. In the event that higher voltage cardioversion or defibrillation pulses are required, microprocessor 224 activates the cardioversion and defibrillation control circuitry 230 to initiate charging of the high voltage capacitors 246 and 248 via charging circuit 236 under the control of high voltage charging control line 240. The voltage on the high voltage capacitors is monitored via a voltage capacitor (VCAP) line 244. When the voltage reaches a predetermined value set by microprocessor 224, a logic signal is generated on the capacitor full (CF) line 254, terminating charging. The defibrillation or cardioversion pulse is delivered to the heart under the control of the timing and control circuitry 212 by an output circuit 234 via a control bus 238. The output circuit 234 determines the electrodes used for delivering the cardioversion or defibrillation pulse and the pulse wave shape.

In one embodiment, the implantable system may additionally include one or more physiological sensors for monitoring hemodynamic or myocardial contractile function or a metabolic status. The physiological sensor may reside within or on the heart, or endo- or extra-arterially for sensing a signal proportional to the hemodynamic function of the heart, myocardial contraction or heart wall motion, and/or a metabolic parameter. As such, IMD 10 is additionally equipped with sensor signal processing circuitry 331 coupled to a terminal 333 for receiving an analog sensor signal. A physiological sensor included in the implanted system may be, but is not limited to, a sensor of flow, pressure, heart sounds, wall motion, cardiac chamber volumes or blood chemistry parameters such as oxygen saturation or pH. Sensor signal data is transferred to microprocessor 224 via data/address bus 218 such that an index of cardiac hemodynamic or contractile performance or a metabolic status may be determined according to algorithms stored in RAM 226. Sensors and methods for determining a cardiac performance index as implemented in the previously-cited '098 patent to Bennett may also be used in conjunction with methods described herein for controlling ESS.

Figure 3:
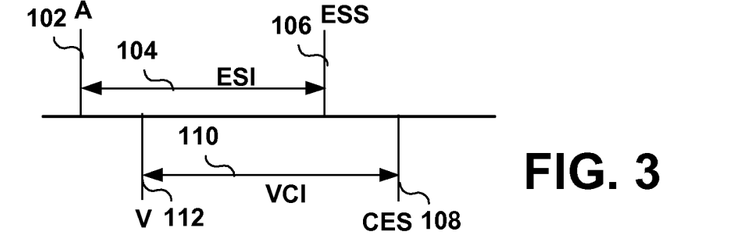
FIG. 3 is a timing diagram illustrating one method for delivering an extra systolic stimulation therapy.

FIG. 3 is a timing diagram illustrating one method for delivering an ESS therapy. An ESI 104 is initiated in response to a primary atrial event 102. The primary atrial event 102 may be an atrial pacing pulse or a sensed P-wave. Upon termination of the ESI, an ESS pulse 106 is delivered to a supraventricular location of the heart. The ESS pulse 106 may be delivered in an atrial chamber or to the His bundle, for example. A depolarization resulting from the ESS pulse is intrinsically conducted to the ventricles causing a conducted extra systole (CES) 108 in the ventricular chambers. The ESI 104 is automatically set by the IMD to produce the conducted extra systole 108 at a desired ventricular coupling interval 110 after a primary ventricular event 112. The primary ventricular event 112 is either a ventricular pacing pulse or a sensed R-wave. Ventricular pacing may include right, left or bi-ventricular pacing.

In past practice, an ESS pulse has typically been delivered in the ventricles upon expiration of an extra systolic interval for achieving PESP effects in the ventricle. ESS delivered in the ventricle could be combined with ESS provided in the atrium for achieving PESP effects in the atrium and the ventricle. Atrial PESP effects might be induced to enhance the atrial contribution to ventricular filling. Thus, in past practice the extra systole was an evoked response to an ESS pulse delivered in the same heart chamber as the evoked extra systole, following a sensed or paced primary systole. As shown in FIG. 3, an extra systolic stimulation pulse 106 is delivered to a supraventricular location in the heart such that the extra systole in the ventricles is always an intrinsically conducted extra systole (CES) 108. The methods used for automatically determining the ESI 104 for controlling the delivery of the supraventricular ESS pulse will depend on the supraventricular delivery site of the ESS pulse 106 and whether the primary ventricular event 112 is a paced or sensed event as well as other considerations as will be described herein.

Figure 4:
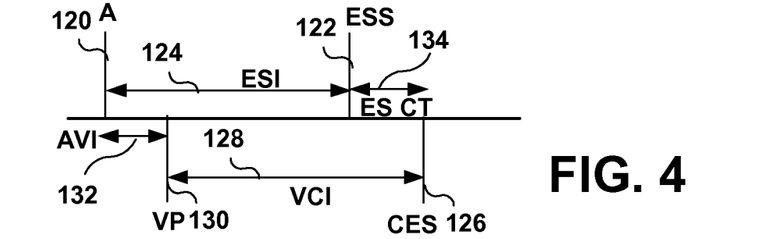
FIG. 4 is a timing diagram illustrating one method for automatically determining an ESI for controlling delivery of a supraventricular extra systolic stimulation (ESS) pulse during ventricular pacing.

FIG. 4 is a timing diagram illustrating one method for automatically determining an ESI for delivering a supraventricular ESS pulse during ventricular pacing. The primary atrial event 120 is followed by an atrial-ventricular interval (AVI) 132 used to control the timing of a ventricular pacing pulse 130 following the primary atrial event 120. The ESI 124 is determined as the sum of the AVI and a desired ventricular coupling interval (VCI) 128 less a measured or estimated extra systolic conduction time (ES CT) 134. This method for automatically determining the ESI considers maintaining an optimal AVI for proper A-V synchrony during the primary systole and adjusting the ESI 124 based on this optimal AVI and a desired ventricular coupling interval 128. If the AVI 132 is an adaptive interval, for example if the AVI 132 changes with changes in an intrinsic or paced atrial rate or is automatically adjusted by the IMD in response to other conditions, the ESI 124 is automatically re-determined as a function of the adaptive AVI 132, the desired ventricular coupling interval 128, and the measured or estimated extra systolic conduction time 134. In this way, the ESI 124 is adjusted as needed to maintain the conducted extra systole 126 at the desired ventricular coupling interval 128 following ventricular pacing pulse 130. An ESS pulse 122 delivered to an atrial location at the expiration of ESI 124 may or may not result in a PESP effect in the atria.

Since the primary ventricular event is a ventricular paced event 130 and the extra systole is an intrinsically conducted event, this method for delivering an ESS therapy may be referred to as a "reverse coupled pacing," in contrast to the past practice of "coupled pacing" wherein the primary ventricular event was a sensed event and the extra systole was a pacing-evoked event, in response to an ESS pulse delivered in the ventricle.

In one embodiment, the desired ventricular coupling interval 128 corresponds to the optimal interval of time between the ventricular pacing pulse 130 and the intrinsically conducted extra systole 126 for achieving a desired PESP effect. The desired ventricular coupling interval 128 may be determined during testing routines directed at determining the interval resulting in a desired PESP effect. The desired ventricular coupling interval may alternatively be determined based on measured or estimated ventricular refractory times, measurements of activation-recovery intervals as generally described in U.S. Pat. Publication No. 2004/0220640 (Burnes et al.), incorporated herein by reference in its entirety, measurements of cardiac hemodynamic performance, or by other methods.

The extra systolic conduction time 134 corresponds to the time for an extra systolic depolarization evoked at the supraventricular ESS pulse delivery site to be conducted to the ventricles. The extra systolic conduction time 134 may be measured by applying a supraventricular ESS pulse and measuring an interval of time between the ESS pulse delivery and a conducted depolarization sensed in the ventricles. The extra systolic conduction time 134 may alternatively be estimated as a function of the primary conduction time for a primary atrial event, paced or sensed, to be intrinsically conducted to the ventricles. It is recognized that measurement of the primary systolic conduction time may not correspond directly to the extra systolic conduction time 134 since the refractoriness of the heart may result in an altered conduction speed. As such, measurements of a primary systolic conduction time may be used for estimating the extra systolic conduction time 134.

In an alternative embodiment, the AVI 132 may be computed based on a desired ESI 124 and a desired ventricular coupling interval 128. The ESI 124 may be optimized to achieve a desired PESP effect in the atrial chambers in response to the supraventricular ESS pulse 122 being delivered to an atrial location. The AVI 132 may then be computed as the sum of the desired ESI 124 and the extra systolic conduction time 134 less the desired ventricular coupling interval 128. A minimum limit to the AVI 132 may be set to prevent early contraction of the ventricles from occurring prior to atrial relaxation and complete ventricular filling. If a computed AVI is determined to be less than a predefined minimum AVI limit, the ESI 124 may be lengthened appropriately such that the AVI 132 can be set at or above the minimum limit. In this embodiment, the AVI 132 may or may not result in optimal coupling between the primary atrial event 120 and the ventricular pacing pulse 130.

Figure 5:
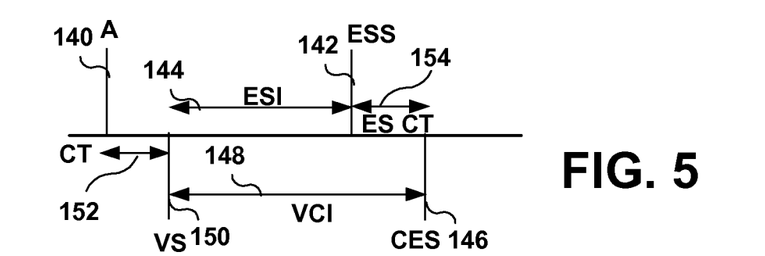
FIG. 5 is a timing diagram of one method for controlling the delivery of a supraventricular ESS pulse during ventricular sensing.

FIG. 5 is a timing diagram of one method for controlling the delivery of a supraventricular ESS pulse during ventricular sensing. A primary atrial event 140 is either sensed or paced and is followed by an intrinsically conducted primary ventricular event 150. The sensed primary ventricular event 150 occurs at an intrinsic conduction time 152 after the primary atrial event 140. Sensing of the primary ventricular event 150 initiates an ESI 144 set equal to the desired ventricular coupling interval 148 less the extra systolic conduction time 154. The extra systolic conduction time 154 may be a previously measured or estimated conduction time as described previously. Upon expiration of the ESI 144, a supraventricular ESS pulse 142 is delivered and is intrinsically conducted to the ventricles to induce the conducted extra systole 146 at the desired ventricular coupling interval 148 following the sensed primary ventricular event 150.

In one embodiment the extra systolic conduction time 154 used in setting ESI 144 is estimated based on a previously measured primary conduction time 152 between the primary atrial and ventricular events 140 and 150. Since the ESS pulse 142 may be delivered at any selected supraventricular location, the extra systolic conduction time 154 may be different than the conduction time 152 between primary events 140 and 150. For example, when the ESS pulse 142 is delivered to the His bundle, the extra systolic conduction time 154 may be estimated as a percentage of the primary conduction time 152 measured between primary atrial and ventricular systolic events 140 and 152. Furthermore, the state of refractoriness of the heart may alter the conduction time for an extra systole as compared to a primary systole.

When the primary atrial event 140 is a paced event and the supraventricular ESS pulse 142 is delivered at the same location as an atrial primary pacing pulse, the extra systolic conduction time 154 may be substantially equal to the primary conduction time 152. As such, the ESI 144 triggered by the primary ventricular sense event 150 may be set to a value corresponding to the desired ventricular coupling interval 148 less a previously measured primary conduction time 152. In still other embodiments, the primary conduction time 152 may be measured on a beat-by-beat basis as the interval between primary atrial event 140 and the primary ventricular event 150 and used for estimating the extra systolic conduction time 154 on a beat-by-beat basis. The ESI 144 set as the ventricular coupling interval 148 less the estimated extra systolic conduction time is then automatically adjusted on a beat-by-beat basis according to measured changes in myocardial conduction.

A supraventricular ESS pulse 142 delivered in the atrium may result in PESP effects in the atrium although the ESI 144 may be optimized to primarily achieve a desired PESP effect in the ventricles. The ESS pulse 142 may alternatively be delivered in the HIS bundle for achieving ventricular PESP effects in response to the intrinsically conducted extra systole 146.

Figure 6:
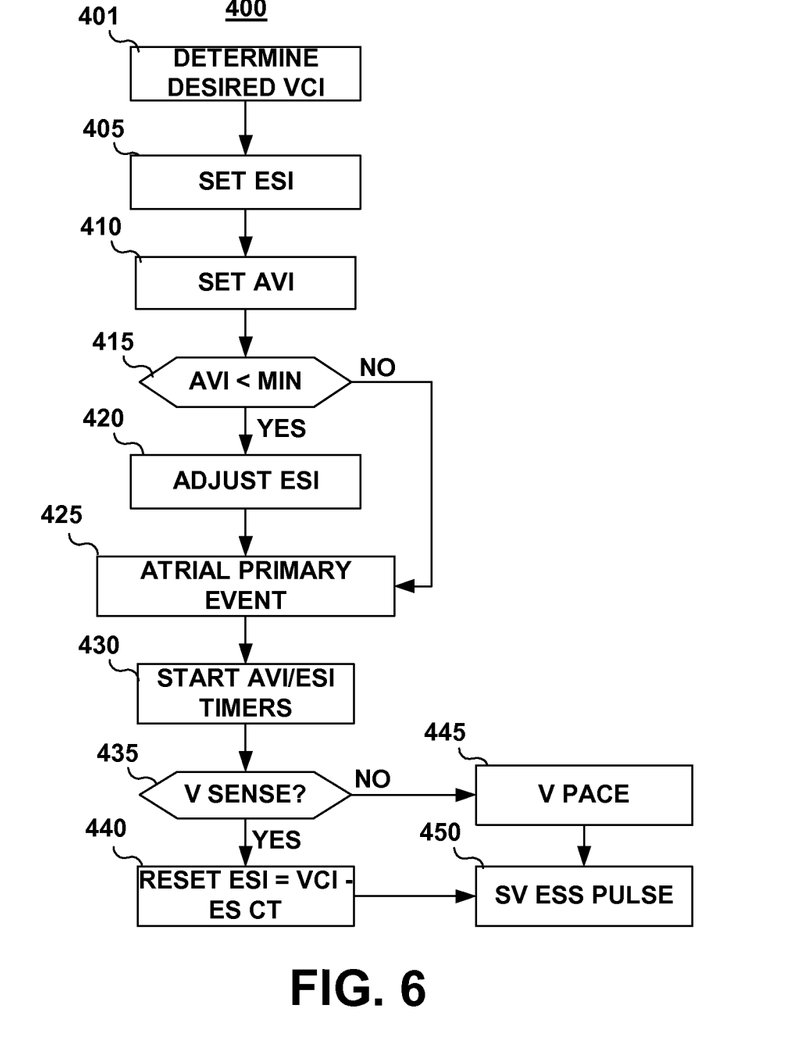
FIG. 6 is a flow chart of a method for controlling the delivery of supraventricular stimulation pulses for inducing intrinsically conducted ventricular extra systoles.

FIG. 6 is a flow chart of a method for controlling the delivery of supraventricular stimulation pulses for inducing intrinsically conducted ventricular extra systoles. Flow chart 400 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern IMD, given the disclosure herein, is within the abilities of one of skill in the art.

Methods described in conjunction with drawings presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 401, a desired ventricular coupling interval is determined. It is recognized that the desired ventricular coupling interval for a paced primary ventricular event may be different than the desired ventricular coupling interval for an intrinsic primary ventricular event. As such, determining the desired ventricular coupling interval at block 401 may include determining and storing ventricular coupling intervals corresponding to each of paced and intrinsic primary ventricular events.

At block 405, an ESI is set for timing the delivery of a supraventricular ESS pulse following a primary atrial event during ventricular pacing. The ESI may be set to achieve a desired PESP effect in the ventricular chambers, with or without a PESP effect in the atria. The ESI may be set in combination with an atrial-ventricular pacing interval (AVI) at block 410 such that both an atrial-ventricular coupling interval and a ventricular coupling interval are optimized. In this case, the AVI is set to a desired value at block 410 and the ESI set at block 405 is set equal to the sum of the AVI and the desired ventricular coupling interval less a measured or estimated extra systolic conduction time as described previously.

Alternatively, the ESI may be set to provide a desired extra systolic coupling interval in both the atrium and in the ventricles. In this case, the AVI is set at block 410 as the sum of the ESI set at block 405 and a measured or estimated extra systolic conduction time less the desired ventricular coupling interval. A minimum AVI may be predefined to prevent early ventricular activation. If an AVI is determined be less than a minimum AVI, at block 415, the ESI is adjusted to allow the AVI to be set to at least the minimum AVI at block 420.

At block 425, a primary atrial event occurs, which may be a sensed intrinsic event (P-wave) or a paced event. An ESI timer and an AVI timer are started at block 430 in response to the primary atrial event. If the AVI expires prior to sensing a ventricular event at block 435, a primary ventricular pacing pulse is delivered at block 445. A supraventricular (SV) ESS pulse is then delivered at block 450 upon expiration of the ESI timer such that an evoked extra systolic depolarization is intrinsically conducted from the supraventricular location to the ventricles and occurs at the desired ventricular coupling interval relative to the ventricular pacing pulse.

If an intrinsic ventricular event is sensed at block 435, the ESI may be automatically reset at block 440 such that the supraventricular ESS pulse can be delivered relative to the intrinsic primary ventricular event. As such, the ESI timer is reset at block 440 in response to the sensed ventricular event, to a time interval equal to the desired ventricular coupling interval less a measured or estimated extra systolic conduction time (as generally described in conjunction with FIG. 5). Upon expiration of the reset ESI timer, a supraventricular ESS pulse is delivered at block 450 such that the evoked depolarization is intrinsically conducted to the ventricles and the conducted extra systole occurs at the desired coupling interval relative to the ventricular sensed event. All or portions of method 400 may be repeated on a beat-by-beat or less frequent basis for controlling the delivery of an ESS therapy.

Figure 7:
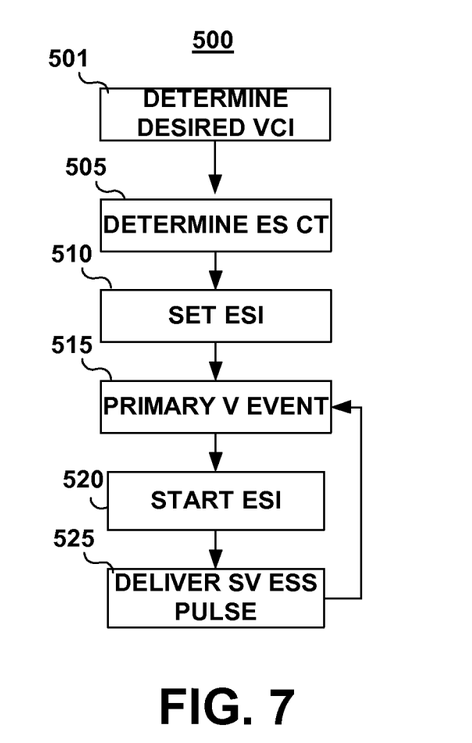
FIG. 7 is a flow chart of an alternative method for controlling extra systolic stimulation.

FIG. 7 is a flow chart of an alternative method for controlling extra systolic stimulation. Method 500 controls delivery of a supraventricular ESS pulse based on detection of a primary ventricular event without regard for the timing of atrial events. At block 501, a desired ventricular coupling interval is determined. At block 505, an extra systolic conduction time is measured or estimated. The ESI is then set at block 510 as the desired ventricular coupling interval less the extra systolic conduction time. Upon detecting a primary ventricular event, which may be a paced event, an intrinsic R-wave or an evoked R-wave, the ESI timer is started at block 520. Upon expiration of the ESI, a supraventricular ESS pulse is delivered at block 525. Method 500 may be repeated by returning to block 515 to wait for the next primary ventricular event such that ESS is delivered on a beat-by-beat basis, i.e. with every primary ventricular event, or at another ratio relative to the primary ventricular rate.

Figure 8:
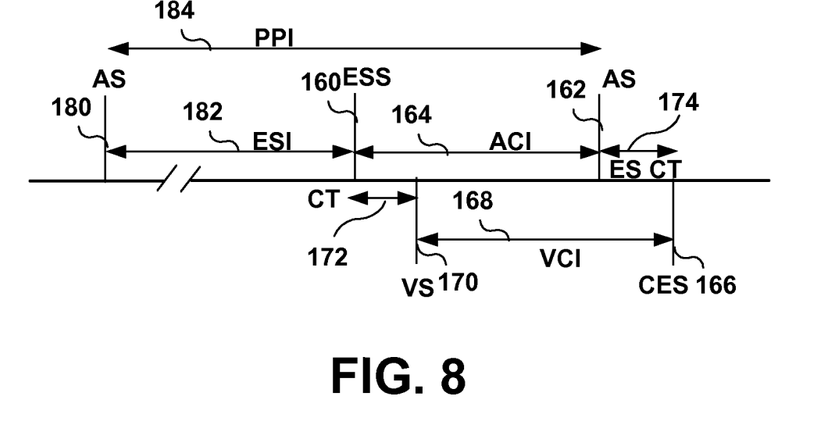
FIG. 8 is a timing diagram illustrating an alternative method for delivering an extra systolic therapy.

FIG. 8 is a timing diagram illustrating an alternative method for delivering an extra systolic therapy. In this embodiment, the extra systolic stimulation pulse 160 is delivered to a supraventricular stimulation site prior to an intrinsic atrial sensed event (AS) 162. Atrial sense event 162 corresponds to an intrinsic depolarization, e.g. initiated by the sino-atrial node, during a normal sinus rhythm. The ESS pulse 160, in this case, is delivered prior to the intrinsic atrial event 162, rather than after the intrinsic event 162, at a time corresponding to a desired ESI 164. In this way, the intrinsic atrial event effectively becomes the "extra systole" and the ESS pulse 160 effectively becomes the "primary systole."

An evoked depolarization resulting from the ESS pulse 160 is conducted to the ventricles resulting in the "primary" ventricular sense event 170 following a primary conduction time 172. The conduction time 172 corresponds to the time required for the evoked depolarization to conduct from the supraventricular stimulation site to the ventricles.

The intrinsic atrial sense event 162 will be conducted to the ventricle via the normal conduction pathway to cause the conducted extra systole (CES) 166 in the ventricles. The CES 166 occurs in the ventricle following an extra systolic conduction time (ES CT) 174 corresponding to the time required for the intrinsic AS 162 to be conducted to the ventricles. The conducted extra systole 166 occurs after the primary ventricular sense event 170 at a desired ventricular coupling interval 168. As such, in this embodiment the ESS pulse 160 is delivered at an atrial coupling interval (ACI) 164 prior to an intrinsic atrial sense 162.

Delivery of the ESS pulse 160 is controlled by starting an ESI 182 upon sensing a previous atrial sense event 180. The ESI 182 may be determined based on a desired atrial coupling interval 164 and/or a desired ventricular coupling interval 168. In one embodiment, the ESI 182 is set based on an estimated intrinsic atrial interval (PPI) 184 less an estimated or measured extra systolic conduction time 174, less a desired atrial coupling interval 164. The desired atrial coupling interval 164 may correspond to a desired PESP effect in the atrial chambers or determined as a function of a desired ventricular coupling interval 168. For example, the atrial coupling interval 164 may be determined as a desired ventricular coupling interval 168 less a measured or estimated extra systolic conduction time 174 plus a measured or estimated primary conduction time 172. The desired ventricular coupling interval 168 may be selected for achieving a desired PESP response in the ventricles as described previously.

The intrinsic atrial PP interval 184 may be estimated from a previously sensed atrial rhythm. For example, a desired number of preceding atrial sinus intervals, for example 10 previous intervals, may be measured and averaged to estimate the PPI 184. As such, the ESI 182 may be automatically adjusted to account for changes in a sensed atrial rate as well as changes in measured or estimated primary conduction time 172 and extra systolic conduction time 174.

Figure 9:
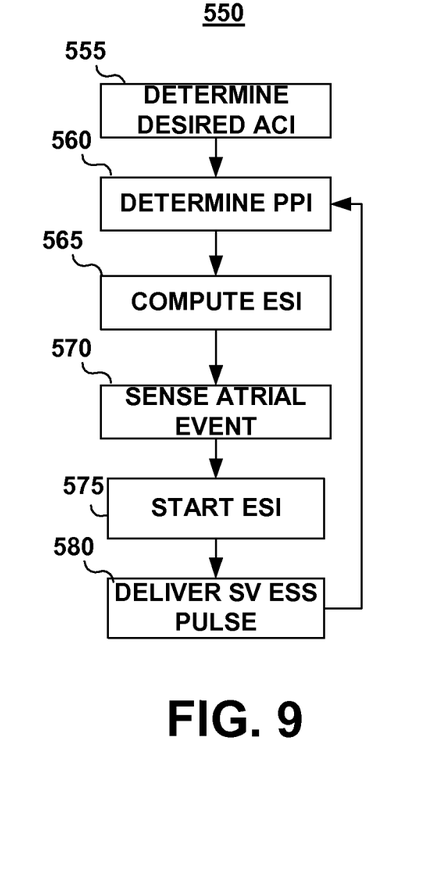
FIG. 9 is a flow chart of a method for controlling an extra systolic therapy wherein the extra systolic stimulation pulse is delivered to a supraventricular site prior to an intrinsic atrial sensed event.

FIG. 9 is a flow chart of a method for controlling an extra systolic therapy wherein the extra systolic stimulation pulse is delivered to a supraventricular site prior to an intrinsic atrial sensed event. At block 555, a desired atrial coupling interval is determined. As described above, the desired atrial coupling interval may be based on achieving a desired atrial PESP effect and/or a desired ventricular PESP effect. As such, the determination of the desired atrial coupling interval at block 555 may include determining a desired ventricular coupling interval as well as measuring or estimating primary and extra systolic conduction times as described previously.

At block 560, a PP interval is estimated or predicted based on an ongoing atrial sinus rhythm. As such, determination of the PP interval at block 560 may include sensing and verifying an atrial sinus rhythm, measuring a predetermined number of atrial sinus intervals, and computing a predicted atrial PP interval using the measured atrial sinus intervals. The predicted PP interval and the desired atrial coupling interval are used at block 565 to compute an ESI as described above in conjunction with FIG. 8. Upon sensing the next intrinsic atrial event at block 570, an ESI timer is started at block 575. A supraventricular ESS pulse is delivered at block 580 upon expiration of the ESI timer. The ESS pulse may be delivered to any supraventricular location including an atrial location or the bundle of His. The computation of the ESI will take into account the selected ESS delivery site.

Method 550 may be repeated by returning to block 560 for automatically re-determining a PP interval and automatically adjusting the ESI at block 565 on a beat-by-beat or less frequent basis. Alternatively, method 550 may return to block 570 to monitor for the next atrial event to restart the ESI timer at block 575. The ESI may be adjusted by returning to block 555 or block 560 on a periodic basis.

Examples

The following examples are intended to assist understanding of various exemplary aspects of the instant invention and should not be viewed in any way as limited the invention to any particular embodiments.

1. A computer-readable medium for storing a set of instructions which when implemented in a system cause the system to:
    determine a first coupling interval;
    determine an extra systolic interval in response to the first coupling interval;
    determine a cardiac event;
    initiate the extra systolic interval in response to the cardiac event; and
    deliver a supraventricular stimulation pulse upon expiration of the extra systolic interval,
    wherein the supraventricular stimulation pulse evokes a depolarization conducted to a ventricular chamber occurring at a ventricular coupling interval relative to a ventricular event.

A computer-readable medium according to example 1, wherein the supraventricular stimulation pulse being delivered to a portion of a patient's His bundle.

2. A computer-readable medium according to example 1 wherein the supraventricular stimulation pulse being delivered to an atrium.

3. A computer-readable medium according to example 1 wherein the extra systolic interval being determined so as to induce post-extra systolic potentiation in the atrium.

4. A computer-readable medium according to example 1 wherein the extra systolic interval being determined so as to induce post-extra systolic potentiation in the ventricle.

5. A computer-readable medium according to example 1 wherein determining the cardiac event comprises determining one of an atrial paced event and an atrial sensed event;
    wherein the extra systolic interval being equal to the first coupling interval; and
    wherein the supraventricular stimulation pulse evoking an atrial extra systole subsequent to the determined cardiac event.

6. A computer-readable medium according to example 1 wherein determining the cardiac event comprises determining an atrial sensed event;
    wherein determining the extra systolic interval comprises determining an atrial PP interval, and
    wherein the supraventricular stimulation pulse evoking a primary atrial systole at the first coupling interval prior to a next atrial sensed event.

7. A computer-readable medium according to example 1 wherein determining the first coupling interval comprises determining a desired ventricular coupling interval.

8. A computer-readable medium according to example 1 wherein the ventricular event being a ventricular pacing pulse and further comprising instructions which cause the system to:
    determine the cardiac event as one of an atrial paced event and an atrial sensed event;
    set an atrial-ventricular pacing interval (AVI) in response to the cardiac event; and
    deliver the ventricular pacing pulse upon expiration of the AVI.

9. A computer-readable medium according to example 8 further comprising instructions which cause the system to determine an extra systolic conduction time for use in setting at least one of the AVI and the extra systolic interval.

10. A computer-readable medium according to example 8 wherein the extra systolic interval and being set as a function of the AVI, a desired ventricular coupling interval and the extra systolic conduction time.

11. A computer-readable medium according to example 8 wherein the AVI being set as a function of a desired ventricular coupling interval, the extra systolic interval and the extra systolic conduction time.

12. A computer-readable medium according to example 9 wherein instructions for causing the system to determine the extra systolic conduction time include instructions for measuring one of a previous extra systolic conduction time and a previous primary conduction time.

13. A computer-readable medium according to example 1 wherein the cardiac event being a sensed ventricular event and wherein instructions for causing the system to set the extra systolic interval include instructions for determining an extra systolic conduction time.

14. A computer-readable medium according to example 13 wherein the extra systolic interval being set as a function of a desired ventricular coupling interval and the extra systolic conduction time.

15. A computer-readable medium according to example 13 wherein determining the extra systolic conduction time includes measuring one of a previous extra systolic conduction time and a previous primary conduction time.

16. A computer-readable medium according to example 13 wherein determining the extra systolic conduction time includes measuring a primary conduction time between an atrial event and the ventricular event.

17. A computer-readable medium according to example 8 wherein delivering the ventricular pacing pulse includes delivering biventricular pacing.

18. A computer-readable medium according to example 8 wherein the cardiac event being one of a paced atrial event and a sensed atrial event.

19. A medical device, comprising:
   an electrode adapted for deployment to a supraventricular stimulation site;
   pulse generating circuitry coupled to the electrode for generating extra systolic stimulation pulses;
   a control module configured to determine a first coupling interval, set an extra systolic interval in response to the first coupling interval; and for controlling the pulse generating circuitry to deliver an extra systolic stimulation pulse to the supraventricular stimulation site upon expiration of the extra systolic interval,
   wherein the supraventricular stimulation pulse evokes a depolarization conducted to a ventricular chamber occurring at a ventricular coupling interval relative to a ventricular event.

20. A device according to example 19 wherein the supraventricular stimulation pulse being delivered to a His bundle.

21. A device according to example 19 wherein the supraventricular stimulation pulse being delivered to an atrium.

22. A device according to example 19 wherein the extra systolic interval being set so as to induce post-extra systolic potentiation in the atrium.

23. A device according to example 19 wherein the extra systolic interval being set so as to induce post-extra systolic potentiation in the ventricle.

24. A device according to example 19 wherein the control module being further configured to determine a cardiac event as one of an atrial paced event and an atrial sensed event; and
   Initiate the extra systolic interval in response to the cardiac event;
   wherein the extra systolic interval being equal to the first coupling interval; and
   wherein the supraventricular stimulation pulse evoking an atrial extra systole subsequent to the determined cardiac event.

25. A device according to example 19 wherein the control module being further configured to determine a cardiac event as an atrial sensed event; and
   initiate the extra systolic interval in response to the cardiac event;
   wherein determining the extra systolic interval comprises determining an atrial PP interval, and
   wherein the supraventricular stimulation pulse evoking a primary atrial systole at the first coupling interval prior to a next atrial sensed event.

26. A device according to example 19 wherein determining the first coupling interval comprises determining a desired ventricular coupling interval.

27. A device according to example 19 further comprising an electrode adapted for deployment to a ventricular stimulation site and wherein the control module being further configured to:
   determine a cardiac event as one of an atrial pace event and an atrial sense event;
   set an atrial-ventricular pacing interval (AVI) in response to the cardiac event; and
   control the pulse generating circuitry to deliver a ventricular pacing pulse upon expiration of the AVI wherein the ventricular event being the ventricular pacing pulse.

28. A device according to example 27 wherein the control module being further configured to determine an extra systolic conduction time for use in setting at least one of the AVI and the extra systolic interval.

29. A device according to example 28 wherein the extra systolic interval being initiated in response to the cardiac event and being set as a function of the AVI, a desired ventricular coupling interval and the extra systolic conduction time.

30. A device according to example 28 wherein the extra systolic interval being initiated in response to the cardiac event and wherein the AVI being set as a function of a desired ventricular coupling interval and the extra systolic interval and the extra systolic conduction time.

31. A device according to example 28 wherein determining the extra systolic conduction time includes measuring one of a previous extra systolic conduction time and a previous primary conduction time.

32. A device according to example 29 further comprising sensing circuitry for sensing intrinsic cardiac events and wherein the ventricular event being a ventricular sense event and wherein setting the extra systolic interval includes determining an extra systolic conduction time.

33. A device according to example 32 wherein the extra systolic interval being initiated in response to the ventricular sense event and being set as a function of a desired ventricular coupling interval and the extra systolic conduction time.

34. A device according to example 32 wherein determining the extra systolic conduction time includes measuring one of a previous extra systolic conduction time and a previous primary conduction time.

35. A device according to example 32 wherein determining the extra systolic conduction time includes measuring a primary conduction time between an atrial event and the ventricular sense event.

36. A device according to example 27 wherein delivering the ventricular pacing pulse includes delivering biventricular pacing.

Thus, a device and method for delivering an extra systolic stimulation therapy have been presented in the foregoing description with reference to specific embodiments. It is appreciated that various modifications to the referenced embodiments may be made without departing from the scope of the invention as set forth in the following claims.

The invention claimed is:
1. A method of cardiac stimulation using a device comprising a means for delivering atrial stimulation pulses and a means for determining timing of ventricular depolarizations, comprising:

measuring a conduction time between a delivered atrial stimulation pulse and a resultant following ventricular depolarization;

determining a desired coupling interval between ventricular depolarizations and following ventricular extrasystolic depolarizations; and subsequently delivering an atrial pacing pulse following given ventricular depolarizations at intervals following the given ventricular depolarizations equal to the desired coupling interval minus the measured conduction time.

2. A method according to claim 1, wherein the means for determining timing of ventricular depolarizations comprises a ventricular depolarization sensor and wherein the step of measuring the conduction time comprises measuring an interval between a delivered atrial stimulation pulse and a following ventricular depolarization sensed by the ventricular depolarization sensor.

3. A method according to claim 1, further comprising delivering primary atrial stimulation pulses at a desired heart rate and wherein the step of subsequently delivering atrial stimulation pulses comprises delivering atrial stimulation pulses at intervals following given sensed ventricular depolarizations triggered by delivered primary atrial simulation pulses.

4. A method according to claim 1, wherein the means for determining timing of ventricular depolarizations comprises a ventricular stimulation pulse generator, further comprising the step of delivering ventricular stimulation pulses, and wherein:

the step of determining a desired coupling interval comprises determining a desired interval between delivered ventricular stimulation pulses and following ventricular extrasystolic depolarizations; and the step of subsequently delivering atrial stimulation pulses following given ventricular depolarizations comprises delivering atrial stimulation pulses at intervals following given delivered ventricular pacing pulses equal to the desired coupling interval minus the measured conduction time.

5. A method according to claim 4, further comprising delivering atrial stimulation pulses prior to delivering the given ventricular stimulation pulses.

* * * * *